(12) United States Patent
Yen

(10) Patent No.: US 11,841,134 B2
(45) Date of Patent: Dec. 12, 2023

(54) COMPOSITE LIGHTING DEVICE OF SCENT ATOMIZATION MODULE

(71) Applicant: Yu-Wen Yen, New Taipei (TW)

(72) Inventor: Yu-Wen Yen, New Taipei (TW)

( * ) Notice: Subject to any disclaimer, the term of this patent is extended or adjusted under 35 U.S.C. 154(b) by 0 days.

(21) Appl. No.: 18/020,256

(22) PCT Filed: Nov. 26, 2020

(86) PCT No.: PCT/CN2020/131675
§ 371 (c)(1),
(2) Date: Feb. 7, 2023

(87) PCT Pub. No.: WO2022/109899
PCT Pub. Date: Jun. 2, 2022

(65) Prior Publication Data
US 2023/0288053 A1    Sep. 14, 2023

(51) Int. Cl.
*F21V 33/00* (2006.01)
*A61L 9/14* (2006.01)

(52) U.S. Cl.
CPC ............ *F21V 33/0088* (2013.01); *A61L 9/14* (2013.01); *A61L 2209/134* (2013.01)

(58) Field of Classification Search
CPC ... F21V 33/0088; A61L 9/14; A61L 2209/134
See application file for complete search history.

(56) References Cited

U.S. PATENT DOCUMENTS

| 2014/0177224 A1* | 6/2014 | Tsai | F21K 9/238 |
| | | | 362/373 |
| 2020/0041118 A1* | 2/2020 | Sawalski | F21V 23/001 |
| 2020/0085033 A1* | 3/2020 | Rubel | F21K 9/237 |
| 2020/0254131 A1* | 8/2020 | Sevy | A61L 9/14 |
| 2023/0096168 A1* | 3/2023 | Sward | A61L 9/14 |
| | | | 239/1 |

* cited by examiner

*Primary Examiner* — Christopher E Dunay
(74) *Attorney, Agent, or Firm* — Leong C. Lei

(57) ABSTRACT

The light device with integrated scent atomization module includes a lighting module, a scent atomization module, and an airflow module. The lighting module includes a lighting element producing light, a socket element to a side of the lighting element, and a cap element to a side of the socket element. The scent atomization module is detachably joined to the socket element, and includes an atomizer, and a container adjacent to the atomizer. The airflow module is configured inside the lighting module. The composite lighting device can be mounted to an ordinary lamp socket and substituted for an ordinary light bulb. Through the scent atomization module's atomization of the essential oil stored in the container, scent is released outside of the composite lighting device to achieve air purification. The heat from the lighting element may also accelerate and make more fully the atomization of the scent atomization module.

7 Claims, 10 Drawing Sheets

COMPOSITE LIGHTING DEVICE OF SCENT ATOMIZATION MODULE

BACKGROUND OF THE INVENTION

(a) Technical Field of the Invention

The present invention is generally related to lighting devices, and more particular to a composite lighting device integrated with a scent atomization module.

(b) Description of the Prior Art

There are commercially available scent diffusers that are integrated with lamps, where the heat from the lamps' light source is used to evaporate essential oil. Usually, the essential oil for these devices are manually added into a container not securely sealed, and, therefore, often splits outside the container, raising the hazard of fire accident.

In addition, the essential oil is usually stored outside or around the lamp and the extraction or utilization of lamp heat is less satisfactory.

Furthermore, these devices are usually powered through an external adaptor plugged into a wall socket. This implies that these devices are not convenient to be placed in a higher place and the effect of scent diffusion is compromised.

SUMMARY OF THE INVENTION

To obviate the above shortcomings, the present invention teaches a novel composite lighting device integrated with a scent atomization module.

A major objective of the present invention is to teach a composite lighting device that may be mounted to an ordinary lamp socket for enhanced convenience, in addition to providing both lighting and scent diffusing simultaneously.

To achieve the objective, the composite light device with integrated scent atomization module includes a lighting module, a scent atomization module, and an airflow module. The lighting module includes a lighting element producing light, a socket element to a side of the lighting element, and a cap element to a side of the socket element. The scent atomization module is detachably joined to the socket element, and includes an atomizer, a container adjacent to the atomizer. The lighting module is further configured with one or more slit openings, and a scent outlet. The airflow module is configured inside the lighting module.

Through the cap element, the composite lighting device can be mounted to a powered lamp socket. By drawing electricity from the powered lamp socket, the lighting element produces light and may be substituted for an ordinary light bulb. The airflow module draws air through the slit openings to the scent atomization module. Together with the atomizer's atomization of the essential oil stored in the container, the scent is then released outside of the composite lighting device through the scent outlet to achieve air purification.

The composite lighting device may be installed onto a lamp socket on the ceiling so that the scent may drift downward to achieve better diffusing effect. The heat from the lighting element may also accelerate and utilize more fully the atomization of the scent atomization module.

The foregoing objectives and summary provide only a brief introduction to the present invention. To fully appreciate these and other objects of the present invention as well as the invention itself, all of which will become apparent to those skilled in the art, the following detailed description of the invention and the claims should be read in conjunction with the accompanying drawings. Throughout the specification and drawings identical reference numerals refer to identical or similar parts.

Many other advantages and features of the present invention will become manifest to those versed in the art upon making reference to the detailed description and the accompanying sheets of drawings in which a preferred structural embodiment incorporating the principles of the present invention is shown by way of illustrative example.

DETAILED DESCRIPTION OF THE PREFERRED EMBODIMENTS

The following descriptions are exemplary embodiments only, and are not intended to limit the scope, applicability or configuration of the invention in any way. Rather, the following description provides a convenient illustration for implementing exemplary embodiments of the invention. Various changes to the described embodiments may be made in the function and arrangement of the elements described without departing from the scope of the invention as set forth in the appended claims.

Figure 1:
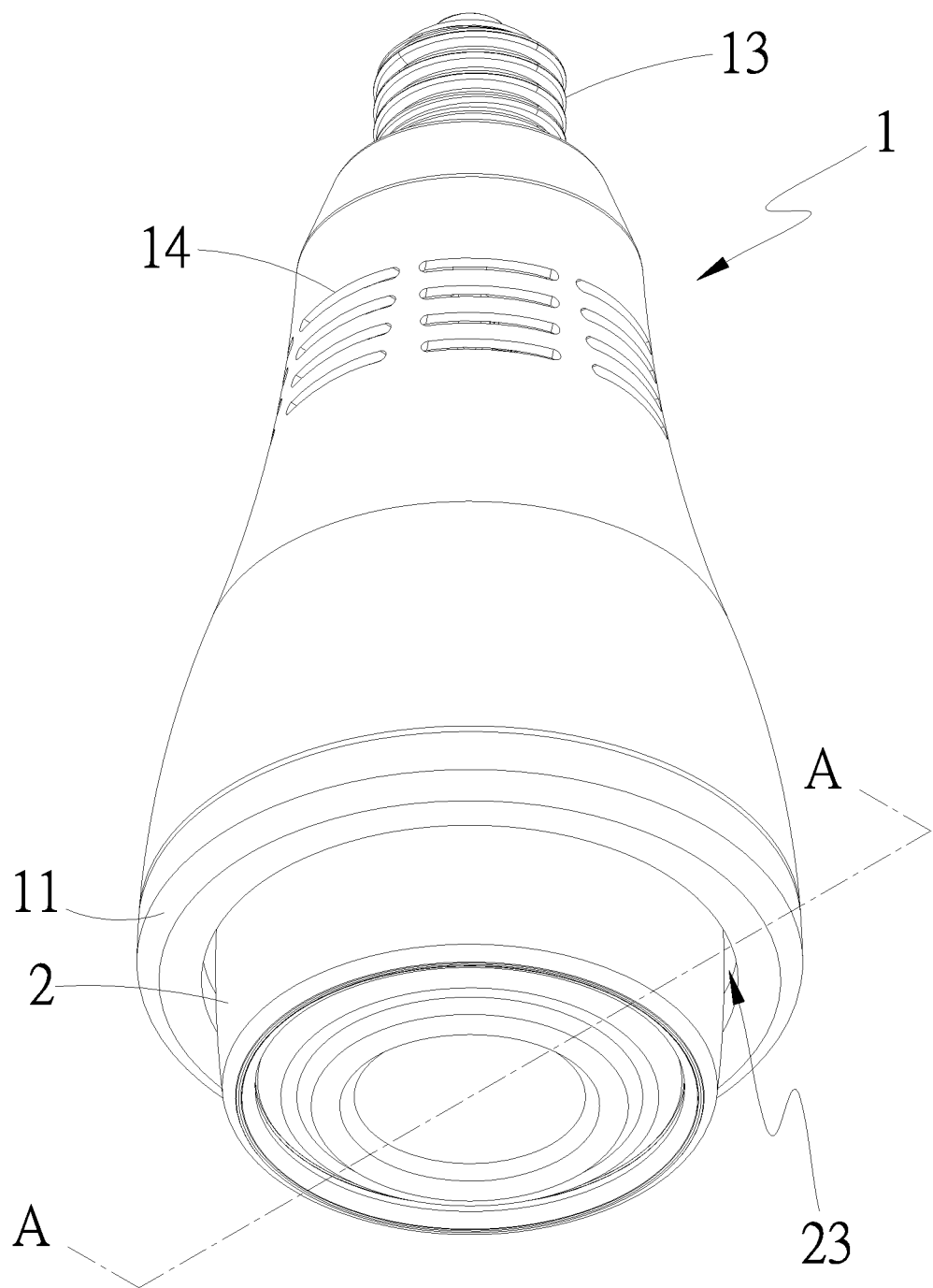
FIG. 1 is a perspective diagram showing a composite lighting device with integrated scent atomization module according to a first embodiment of the present invention.
Figure 2:
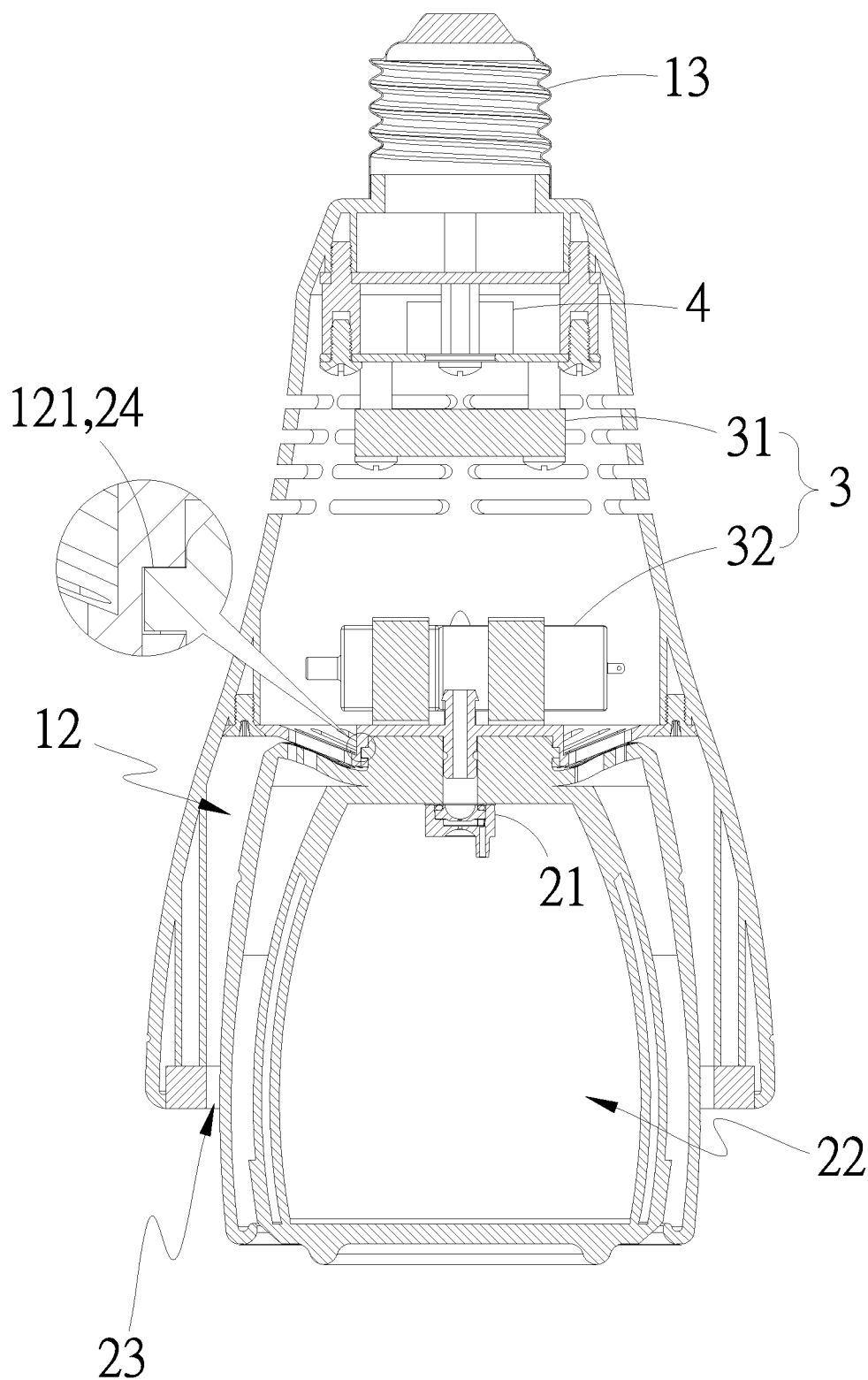
FIG. 2 is a sectional diagram showing the composite lighting device with integrated scent atomization module along the A-A line of FIG. 1.
Figure 3:
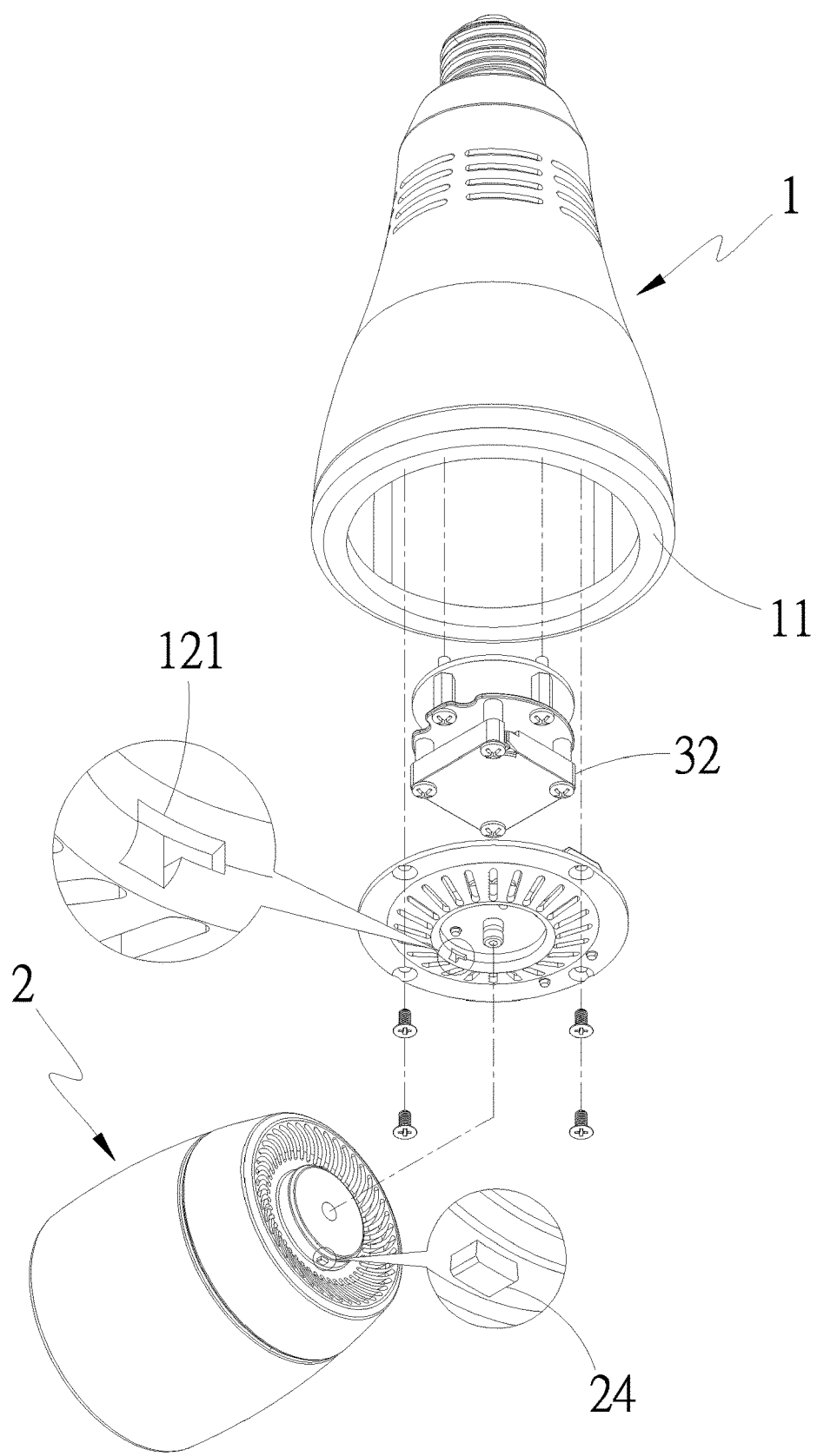
FIG. 3 is a perspective diagram showing a step of the assembly of the composite lighting device with integrated scent atomization module of FIG. 1.
Figure 4:
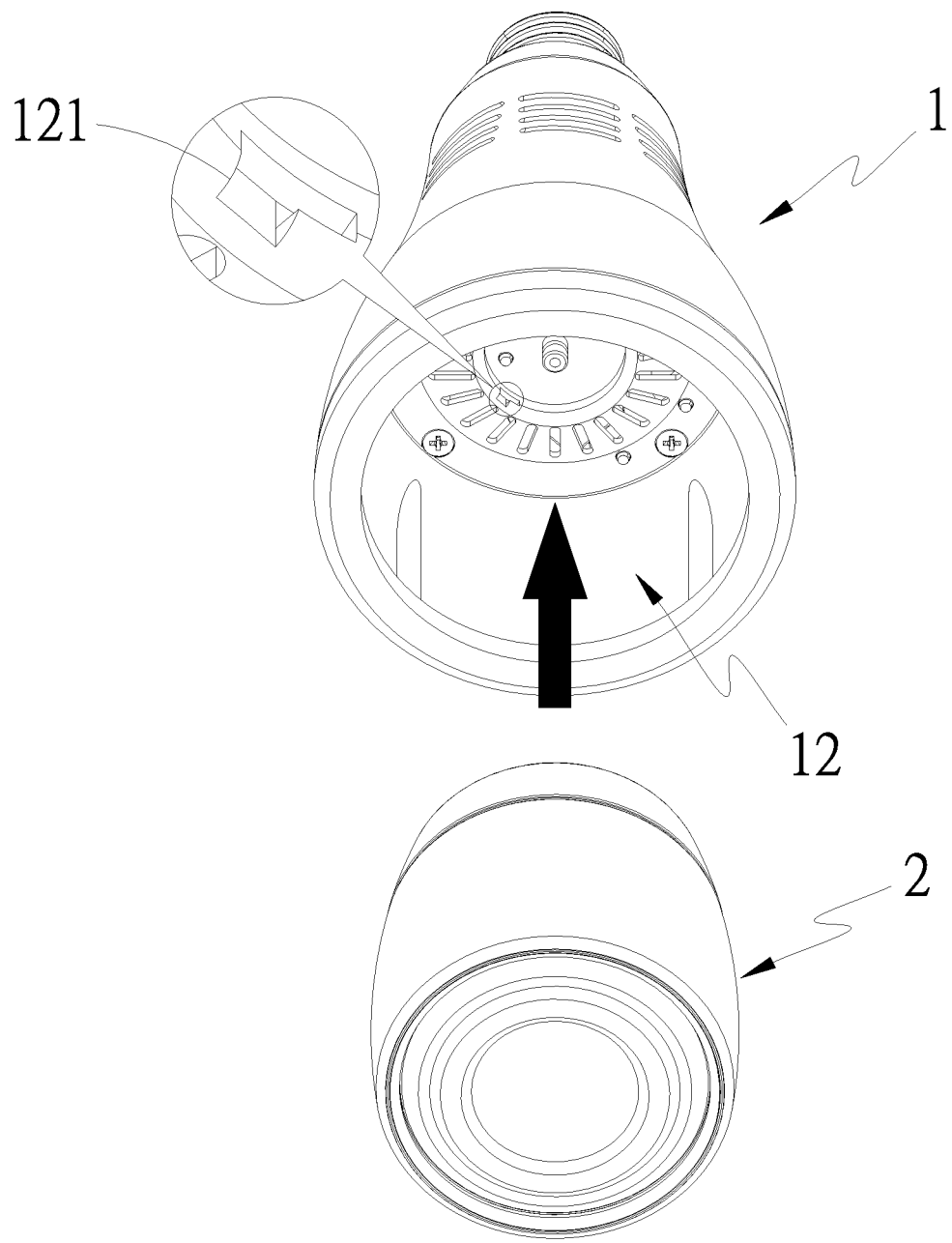
FIG. 4 is a perspective diagram showing a second step of the assembly of the composite lighting device with integrated scent atomization module of FIG. 1.
Figure 5:
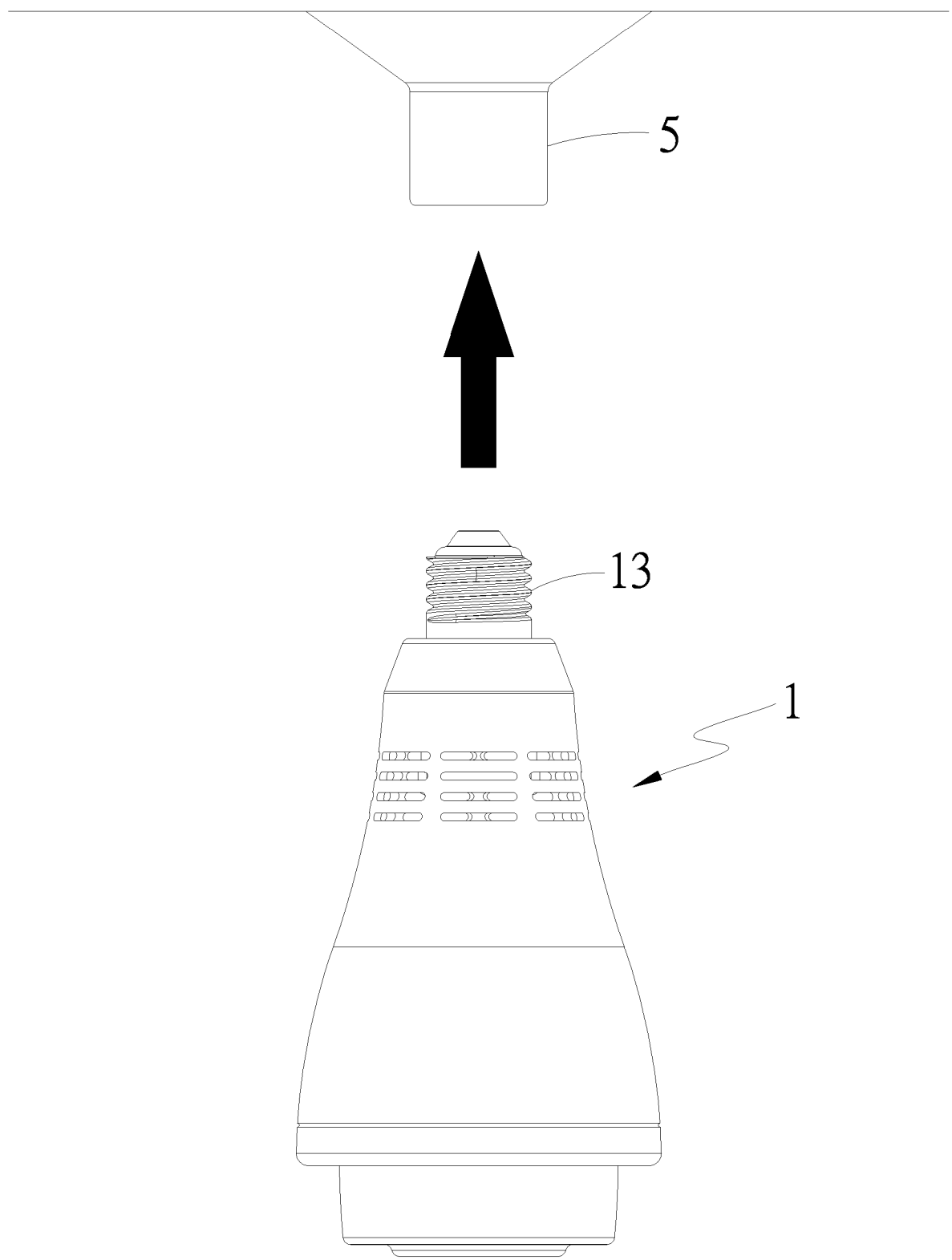
FIG. 5 is a perspective diagram showing a third step of the assembly of the composite lighting device with integrated scent atomization module of FIG. 1.
Figure 6:
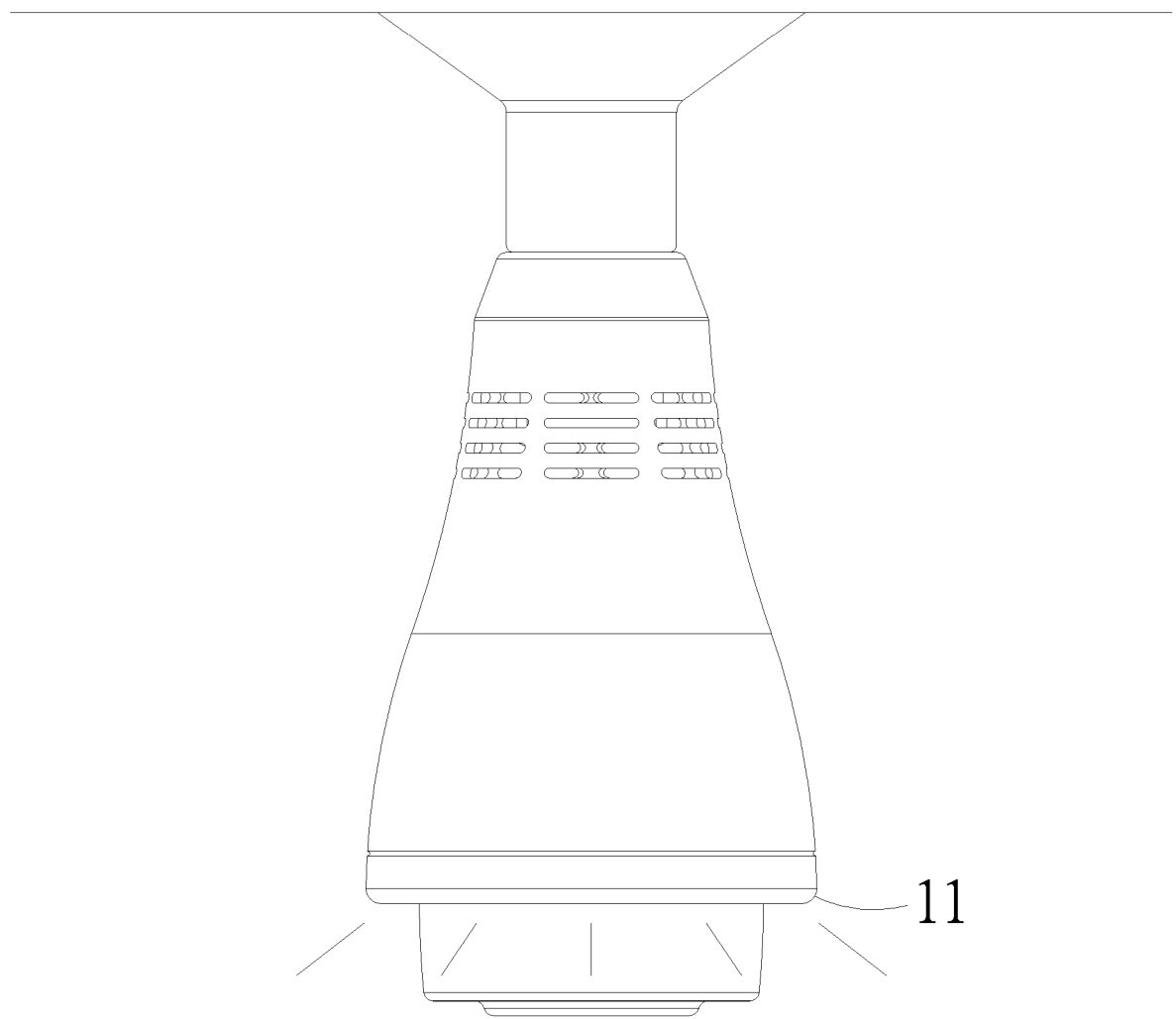
FIG. 6 is a profile diagram showing the composite lighting device with integrated scent atomization module of FIG. 1 producing light.
Figure 7:
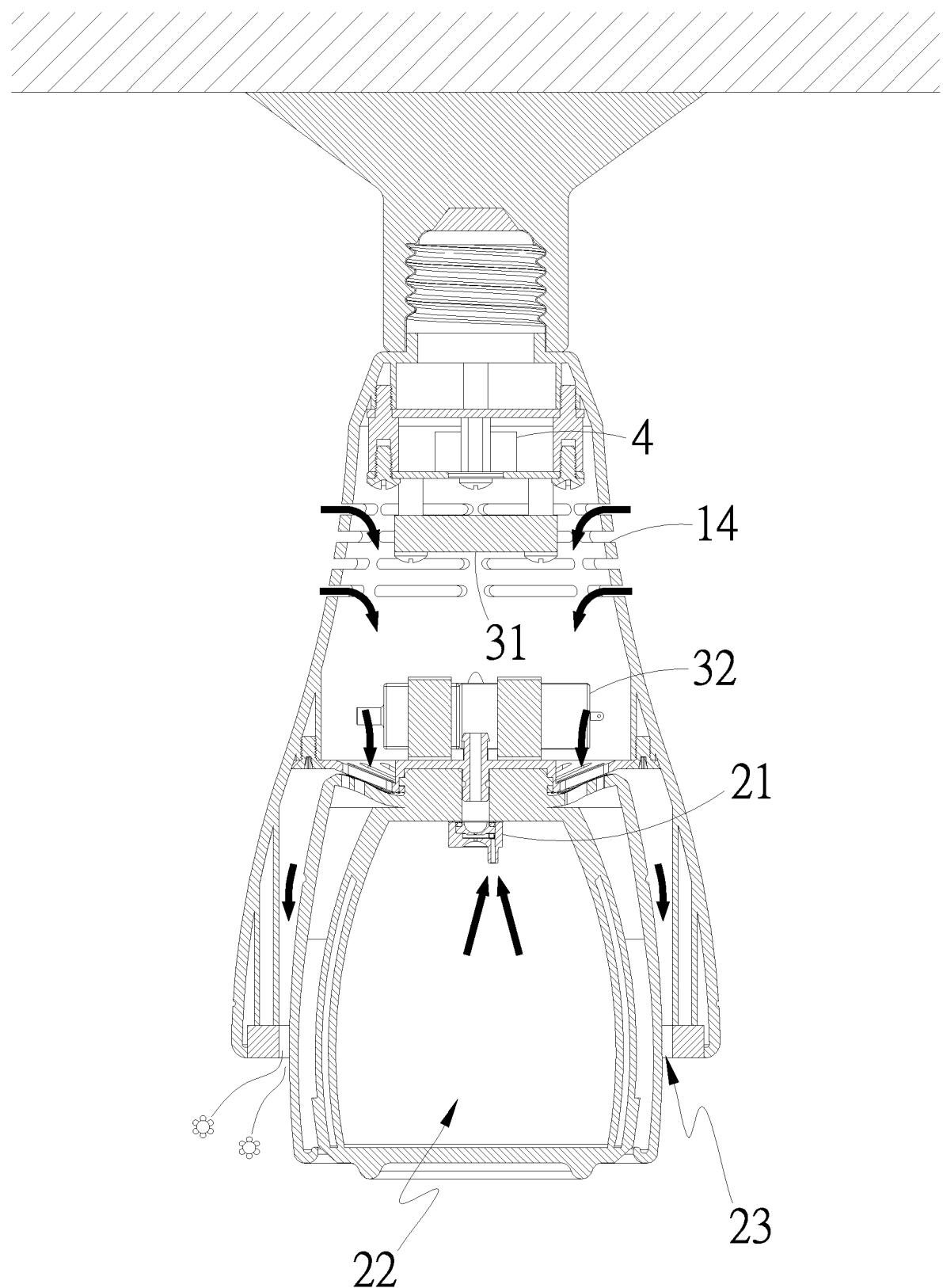
FIG. 7 is a sectional diagram showing the composite lighting device with integrated scent atomization module of FIG. 1 diffusing scent.

As shown in FIGS. 1 to 3, a composite lighting device with integrated scent atomization module according to a first embodiment of the present invention includes the following components.

Alighting module 1 projects light toward a direction. The lighting module 1 includes a lighting element 11 for producing light, a socket element 12 configured to a bottom side of the lighting element 11, and a cap element 13 configured to a top end of the lighting element 11. The cap element 13 is for plugging the composite lighting device to a powered lamp socket. In the present embodiment, the socket element 12 concaves into the bottom side of the lighting element 11 where a scent atomization module 2 is partially or entirely embedded into the lighting element 11.

The scent atomization module 2 is detachably embedded into the socket element 12, and includes an atomizer 21 and a container 22 joined to the atomizer 21. In the present embodiment, at least a first fastener 121 is provided on a side of the socket element 12. Correspondingly, at least a second fastener 24 is configured on the scent atomization module 2 for coupling the first fastener 121. The atomizer 21 includes a Venturi tube mechanism for atomizing the essential oil stored in the container 22.

A scent outlet 23 is provided on the lighting module 1 adjacent to the container 22.

One or more slit openings 14 are configured on the lighting element 11 adjacent to the cap element 13.

An airflow module 3 is configured inside the lighting module 1. The airflow module 3 includes a guiding element 31 and a pump element 32 connected to the guiding element 31.

A power module 4 is configured inside the lighting module 1. The power module 4 is electrically connected to the cap element 13, where electricity drawn from the powered lamp socket is converted and then provided to the lighting element 11.

As shown in FIGS. 1 to 7, to assembly the composite lighting device, the scent atomization module 2 is embedded and secured in the socket element 12 through the mutual engagement of the first fastener 121 and the second fastener 24. The cap element 13 of the composite lighting device is then joined to a powered lamp socket 5. The powered lamp socket 5 may be an ordinary lamp socket on the ceiling. Allowing the composite lighting device to install on an ordinary lamp socket greatly enhances the convenience of the light device.

After the light device is mounted to the powered lamp socket 5, the power module 4 draws electricity from the powered lamp socket 5 and converts it to power the lighting element 11 and the airflow module 3. The lighting element 11 as such produces light for illumination. In the meantime, the guiding element 31 and the pump element 32 of the airflow module 3 start to function. The guiding element 31 draws air through the slit openings 14 and delivers air to the pump element 32. The pump element 32 pressurizes the air into the scent atomization module 2. The air is mixed with the essential oil stored in the container and atomized through the Venturi tube by the atomizer 21. The mixture is then released downward out of the composite lighting device through the scent outlet 23 into the surrounding.

In addition, as the scent atomization module 2 is positioned adjacent to the lighting element 11, the heat from the lighting element 11 accelerates the atomization of the essential oil by the scent atomization module 2. When the essential oil stored in the container 22 is exhausted or is to be replaced, the scent atomization module 2 can be detached, removed, and refilled with new essential oil, thereby achieving enhanced cost reduction and usage convenience.

Figure 8:
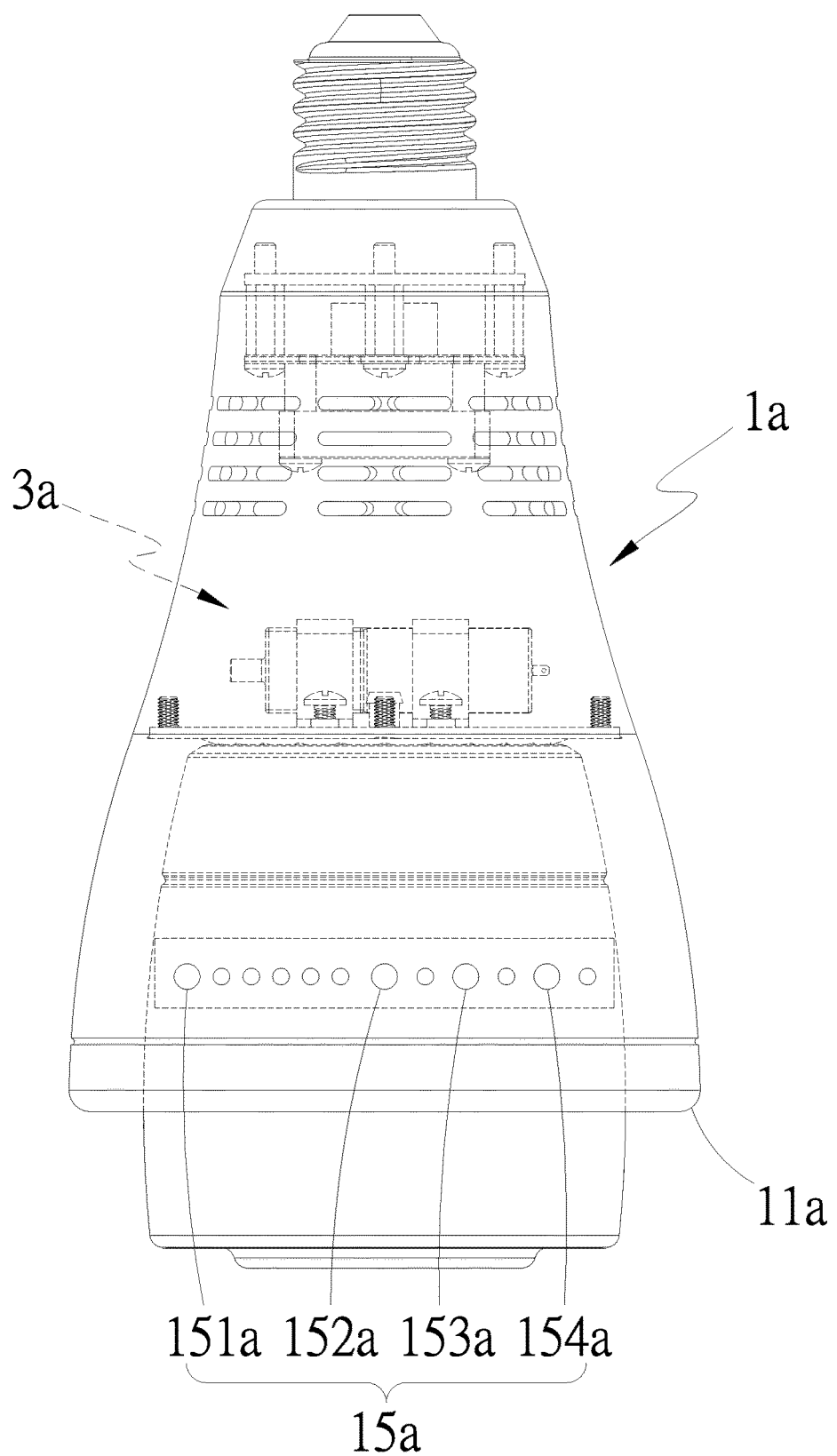
FIG. 8 is a schematic side-view diagram showing a composite lighting device with integrated scent atomization module according to a second embodiment of the present invention controlled by a mobile phone.

As shown in FIG. 8, a second embodiment of the composite lighting device is basically identical to the previous embodiment, except that an operation module 15a is configured on the lighting module 1a data-linked with the lighting element 11a and the airflow module 3a. In the present embodiment, the operation module 15a includes a power switch 151a, a lighting on/off switch 152a, an atomization on/off switch 153a, and atomization strength adjustment switch 154a, through which the operation of the lighting element 11a and the airflow module 3a can be manually controlled and adjusted. However, these switches are exemplary and the present invention is not limited as such.

Figure 9:
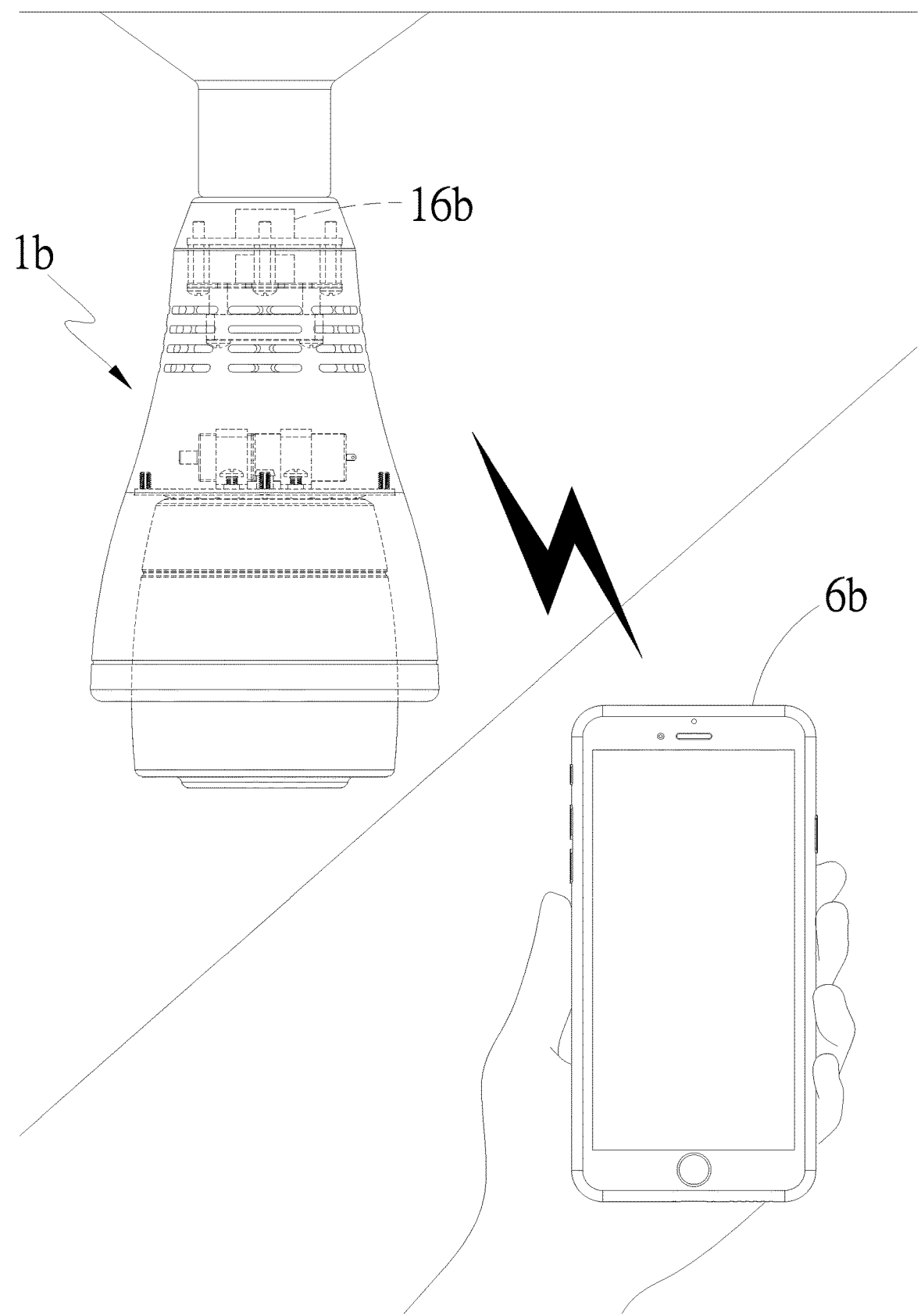
FIG. 9 is a schematic side-view diagram showing a composite lighting device with integrated scent atomization module according to a third embodiment of the present invention controlled by a mobile phone.

As shown in FIG. 9, a third embodiment of the composite lighting device is basically identical to the previous embodiments, except that a wireless connection module 16b is configured inside the lighting module 1b through which the various functions of the operation module described in the previous embodiment can be conducted through a mobile phone 6b in a wireless manner.

Figure 10:
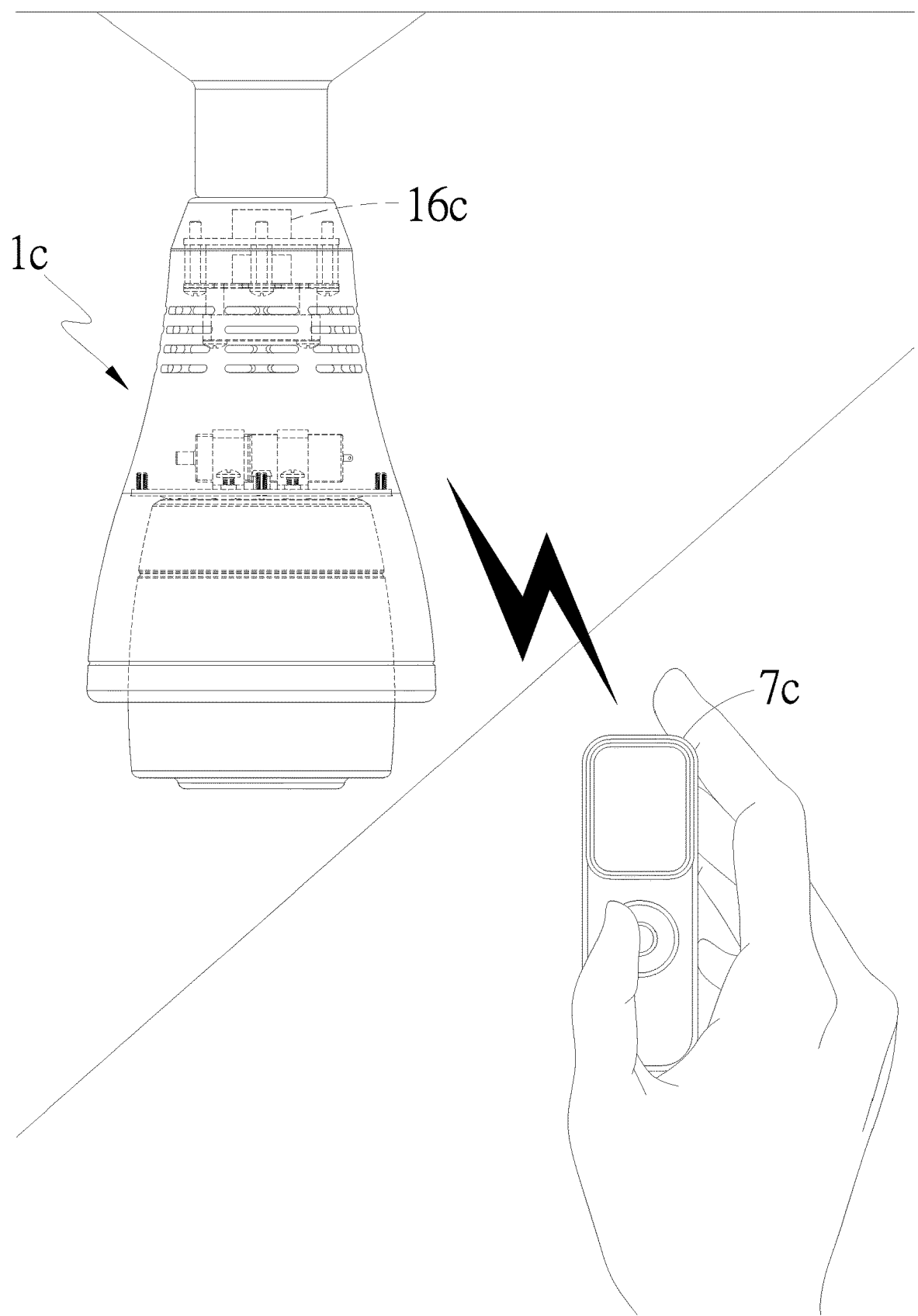
FIG. 10 is a schematic side-view diagram showing a composite lighting device with integrated scent atomization module according to a fourth embodiment of the present invention controlled by a remote controller.

As shown in FIG. 10, a fourth embodiment of the composite lighting device is basically identical to the previous embodiments, except that a wireless connection module 16c is configured inside the lighting module 1c so that the composite lighting device can be wireless-controlled not with a mobile phone 6b but with a remote controller 7c. However, the control of the composite lighting device is not limited to the mobile phone 6b or the remote controller 7c While certain novel features of this invention have been shown and described and are pointed out in the annexed claim, it is not intended to be limited to the details above, since it will be understood that various omissions, modifications, substitutions and changes in the forms and details of the device illustrated and in its operation can be made by those skilled in the art without departing in any way from the claims of the present invention.

I claim:

1. A composite lighting device, comprising:
    a lighting module projecting light toward a direction and comprising a lighting element for producing light, a socket element configured to a bottom side of the lighting element, and a cap element configured to a top end of the lighting element for connection to a powered lamp socket;
    a scent atomization module detachably joined to the socket element and comprising an atomizer, a container joined to the atomizer, and a scent outlet adjacent to the container;
    at least one slit opening configured on the lighting element; and
    an airflow module configured inside the lighting module drawing air from outside the lighting module through the at least one slit opening and delivering air to the scent atomization module;
    wherein the socket element concaves into the bottom side of the lighting element; and a diffuser member is partially or entirely embedded into the lighting element.

2. The composite lighting device according to claim 1, wherein the atomizer comprises a Venturi tube for atomizing liquid stored in the container.

3. The composite lighting device according to claim 1, wherein the airflow module comprises a guiding element and a pump element connected to the guiding element.

4. The composite lighting device according to claim 1, further comprising a power module configured inside the lighting module electrically connected to the cap element, where electricity drawn from the powered lamp socket is converted and then provided to the lighting element.

5. The composite lighting device according to claim 1, further comprising an operation module configured on the lighting module data-linked with the lighting element and the airflow module.

6. The composite lighting device according to claim 1, wherein at least a first fastener is provided on a side of the socket element.

7. The composite lighting device according to claim 6, wherein at least a second fastener is configured on the scent atomization module for coupling the first fastener.

* * * * *